(12) United States Patent
Baranyai

(10) Patent No.: US 8,940,678 B2
(45) Date of Patent: Jan. 27, 2015

(54) METHOD FOR PRODUCING A SOLID WITH SUFFICIENTLY LOW HYGROSCOPICITY WHICH COMPRISES GLUTAMIC ACID-N,N-DIACETIC ACID (GLDA) OR A DERIVATIVE THEREOF

(75) Inventor: Andreas Baranyai, Heitersheim (DE)

(73) Assignee: BASF SE, Ludwigshafen (DE)

( * ) Notice: Subject to any disclaimer, the term of this patent is extended or adjusted under 35 U.S.C. 154(b) by 247 days.

(21) Appl. No.: 13/520,002

(22) PCT Filed: Dec. 27, 2010

(86) PCT No.: PCT/EP2010/007946
§ 371 (c)(1),
(2), (4) Date: Nov. 14, 2012

(87) PCT Pub. No.: WO2011/079940
PCT Pub. Date: Jul. 7, 2011

(65) Prior Publication Data
US 2013/0053296 A1    Feb. 28, 2013

(30) Foreign Application Priority Data
Dec. 30, 2009    (DE) .................. 10 2009 060 814

(51) Int. Cl.
| | |
|---|---|
| C11D 3/20 | (2006.01) |
| C11D 3/33 | (2006.01) |
| C11D 11/00 | (2006.01) |
| C11D 17/06 | (2006.01) |
| C11D 17/00 | (2006.01) |
| C07C 229/12 | (2006.01) |
| C07C 229/24 | (2006.01) |

(52) U.S. Cl.
CPC *C11D 3/33* (2013.01); *C11D 17/06* (2013.01); *C11D 17/0065* (2013.01); *C07C 229/12* (2013.01); *C07C 229/24* (2013.01); *C11D 11/0088* (2013.01); *C11D 17/0039* (2013.01)

USPC .......... 510/349; 510/361; 510/441; 510/445; 510/446; 510/480; 510/488; 510/499; 510/452

(58) Field of Classification Search
CPC .. C11D 3/33; C11D 17/0039; C11D 17/0065; C11D 17/06
USPC ......... 510/349, 361, 441, 445, 446, 480, 488, 510/499
See application file for complete search history.

(56) References Cited

U.S. PATENT DOCUMENTS

| | | | |
|---|---|---|---|
| 3,932,316 A | 1/1976 | Sagel et al. | |
| 5,981,798 A | 11/1999 | Schoenherr et al. | |
| 2009/0082243 A1* | 3/2009 | Brooker et al. | 510/220 |
| 2011/0054215 A1 | 3/2011 | Euser et al. | |
| 2012/0004147 A1* | 1/2012 | Seetz et al. | 507/211 |
| 2012/0068113 A1* | 3/2012 | Giles et al. | 252/186.29 |
| 2012/0149936 A1 | 6/2012 | Baranyai | |
| 2012/0252708 A1* | 10/2012 | Van Lare et al. | 507/241 |
| 2013/0209806 A1* | 8/2013 | Van Lare et al. | 428/404 |

FOREIGN PATENT DOCUMENTS

| | | |
|---|---|---|
| DE | 196 49 681 | 6/1998 |
| DE | 199 37 345 | 2/2001 |
| EP | 0 783 034 | 7/1997 |
| WO | 2009 103822 | 8/2009 |

OTHER PUBLICATIONS

English Language Machine translation of DE 19937345.*
English Language Machine Translation of WO0112768.*
International Search Report Issued May 27, 2011 in PCT/EP10/07946 Filed Dec. 27, 2010.

* cited by examiner

*Primary Examiner* — Gregory R Delcotto
(74) *Attorney, Agent, or Firm* — Oblon, Spivak, McClelland, Maier & Neustadt, L.L.P.

(57) ABSTRACT

The present invention relates to a solid with sufficiently low hygroscopicity which comprises glutamic acid-N,N-diacetic acid (GLDA) or derivatives and/or salts thereof, and a method for its production.

12 Claims, No Drawings

METHOD FOR PRODUCING A SOLID WITH SUFFICIENTLY LOW HYGROSCOPICITY WHICH COMPRISES GLUTAMIC ACID-N,N-DIACETIC ACID (GLDA) OR A DERIVATIVE THEREOF

Glutamic acid-N,N-diacetic acid (GLDA) and salts and/or derivatives thereof are of great interest as complexing agents for alkaline earth metal ions and heavy metal ions in a very wide variety of technical fields of application.

Complexing agents for alkaline earth metal ions and heavy metal ions, as are used for example in detergents and cleaners, are usually synthesized in aqueous solution. For certain application cases, they are required in solid form.

Customary methods for producing solids from solutions are in particular crystallization and spray-drying methods. It is known that crystalline solid, as is produced for example during evaporative or cooling crystallization methods, can comprise water of crystallization and, under ambient conditions, is in most cases less hygroscopic and more storage-stable than amorphous solid. By means of spray-drying methods (e.g. in the spray tower or in the spray fluidized bed), on the other hand, the solid is obtained in amorphous form. In this form, the solid is often highly hygroscopic and, upon open storage under ambient conditions, it loses within a short time the ability to be poured. Consequently, measures to increase the storage stability of spray powders are described in the literature, e.g. the compaction or post-treatment of builders for detergents with benzoic acid in U.S. Pat. No. 3,932,316.

It was an object of the present invention to provide a solid which comprises glutamic acid-N,N-diacetic acid (GLDA) and/or salts or derivatives thereof and which preferably has a sufficiently low hygroscopicity for processing and application.

The present invention relates to a solid which preferably has a sufficiently low hygroscopicity e.g. for processing and application which comprises the following constituents:
a. a core which comprises glutamic acid-N,N-diacetic acid (GLDA) and/or a salt and/or a derivative thereof (in particular glutamic acid-N,N-diacetic acid (GLDA) and/or a salt thereof), and
b. a coating which comprises a compound (or two or more different compounds) of the general formula I

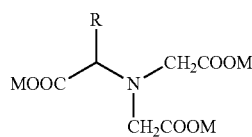

(I)

in which
R is $C_1$- to $C_{30}$-alkyl or $C_2$- to $C_{30}$-alkenyl, which additionally carry, as substituents, up to 5 hydroxyl groups, formyl groups, $C_1$- to $C_4$-alkoxy groups, phenoxy groups or $C_1$- to $C_4$-alkoxycarbonyl groups and can be interrupted by up to 5 nonadjacent oxygen atoms, is alkoxylate groups of the formula —$(CH_2)_k$—O-$(A^1O)_m$-$(A^2O)_n$—Y in which $A^1$ and $A^2$, independently of one another, are 1,2-alkylene groups having 2 to 4 carbon atoms, Y is hydrogen, $C_1$- to $C_{12}$-alkyl, phenyl or $C_1$- to $C_4$-alkoxycarbonyl, and k is the number 1, 2 or 3, and m and n, in each case independently of one another, are numbers from 0 to 50, where the sum of m+n must be at least 4, is phenylalkyl groups having 1 to 20 carbon atoms in the alkyl, a five- or six-membered unsaturated or saturated heterocyclic ring having up to three heteroatoms from the group nitrogen, oxygen and sulfur, which can additionally be benzo-fused, where all of the phenyl rings and heterocyclic rings specified in the meanings for R can also additionally carry, as substituents, up to three to $C_4$-alkyl groups, hydroxyl groups, carboxyl groups, sulfo groups and/or to $C_4$-alkoxycarbonyl groups, or is a radical for the formula

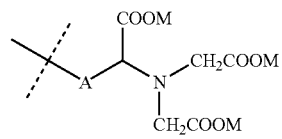

where A is a $C_1$- to $C_{12}$-alkylene bridge or a chemical bond, and
each M, independently of the others, is hydrogen, alkali metal, alkaline earth metal, ammonium or substituted ammonium (e.g. organic amine salts) in the corresponding stoichiometric amounts (in particular each M, independently of the others, is hydrogen, alkali metal, ammonium or substituted ammonium (e.g. organic amine salts) in the corresponding stoichiometric amounts).

The present invention also relates to a method for producing the solid according to the invention, wherein the seed initially introduced is a solid which comprises (or consists of) glutamic acid-N,N-diacetic acid (GLDA) and/or a salt and/or a derivative thereof (in particular glutamic acid-N,N-diacetic acid (GLDA) and/or a salt thereof), and a spray granulation or a coating (preferably in a fluidized-bed apparatus) with at least one compound of the formula I is carried out.

If the core material (which comprises glutamic acid-N,N-diacetic acid (GLDA) and/or a salt and/or a derivative thereof) is used as powder, then this powder, during the spray-granulation, is preferably firstly stuck together by the coating material (which comprises a compound of the general formula I) to give larger particles (granulation), before said particles are coated by the coating material. If the core material is initially introduced in the form of relatively large granules, then these granules, during the spray-granulation, are preferably coated directly with the coating material (coating).

Preferably, the glutamic acid-N,N-diacetic acid (GLDA) and/or the salt is a compound of the formula (II)

$$M^1OOC—(OH_2)_2—CH(COOM^1)\text{-}N(CH_2COOM^1)_2 \quad \text{(II)}$$

where $M^1$ is hydrogen, ammonium or an alkali metal (e.g. sodium, potassium) and/or an organic amine (organic amine salt). Particular preference is given to the L form thereof. Furthermore, preference is given to the sodium salt.

Particular preference is given to compounds of the formula I, as are described in DE 196 49 681.

For the method of the present invention, powders and/or granules of the core material are introduced as initial charge (seeds) in a manner customary per se in a suitable apparatus known per se (preferably a fluidized-bed spray-granulation apparatus, e.g. of the AGT 400 type from Glatt) and fluidized. Here, particle sizes of 30 μm-300 μm (in particular 50 μm-200 μm) for the granulation and 200 μm-1000 μm (in particular 300 μm-1000 μm) for the coating are preferred.

Preferably, the core material (material comprising GLDA) is dry material, i.e. in particular the core material has a water content of less than 10% (in particular less than 5%).

Preferably, the core material (material comprising GLDA) is produced in a manner customary per se by crystallization, spray-drying or by fluidized-bed granulation.

The seeds are held in a fluidized bed in the suspended state (fluidization) and form the surface for a layer-wise drying of atomized droplets which comprise at least one compound of the formula I. The particle produced in this way can be continuously removed from the drying space during the production via a granulation through a classifying discharge in a flexible manner—e.g. with freely adjustable particle sizes—without interrupting the drying operation. In the case of production by means of pure coating, a batch operation is preferred.

As regards the spray-granulation method, see e.g.: H. Uhlemann, L. Mörl, "Wirbelschicht—Sprügranulation [Fluidized-bed—spray-granulation]" Springer—Verlag 2000 (ISBN 3-540-66985-X).

The method of the present invention is one wherein a solid which comprises glutamic acid-N,N-diacetic acid (GLDA) and/or a salt and/or a derivative thereof is initially introduced as seed and then, in a manner customary per se, a spray-granulation/coating with at least one compound of the formula I, which is preferably present in solution (in particular in aqueous solution, preferably ca. 35-43% strength, particularly preferably ca. 35-42% strength, especially preferably ca. 40% strength) is carried out.

Preferably, a spray-granulation/coating with the following parameters is carried out:
preferred incoming air temperature: 90-160° C.,
preferred product temperature: 50-120° C.,
preferred outgoing air temperature: 40-110° C.,
preferred temperature of the feed: 40-100° C.

In the method according to the invention, for example liquid raw material (e.g. a 35 to 43% strength, preferably a 35-42% strength, in particular a 40% strength, aqueous solution of a compound of the formula I) is sprayed onto the seeds (comprising glutamic acid-N,N-diacetic acid (GLDA) and/or a salt and/or a derivative thereof) fluidizing in the stream of hot air, which dries as a result and the seeds are coated or granulated and then coated.

The fluidized-bed apparatus is preferably a fluidized-bed spray-granulator which is equipped for example with a cyclone and/or a filter and/or a wet scrubber.

Here, a solid is referred to as non-hygroscopic or of being of sufficiently low hygroscopicity when, upon open storage under normal ambient conditions, e.g. 25° C. and relative atmospheric humidity of 76%, over a period of at least one day, preferably one week, it keeps its consistency as (preferably free-flowing) powder or granules.

The core of the solid according to the invention comprises glutamic acid-N,N-diacetic acid (GLDA) and/or salt and/or a derivative thereof, preferably a compound of the general formula (II):

$$M^1OOC—(CH_2)_2—CH(COOM^1)-N(CH_2COOM^1)_2 \quad (II)$$

where $M^1$ is hydrogen, ammonium, an organic amine or an alkali metal (preferably sodium). Particularly preferably, the core comprises L-glutamic acid-N,N-diacetic acid tetrasodium salt ($C_9H_9NO_8Na_4$, e.g. CAS No.: 51981-21-6). Preferably, the core material comprises Dissolvine® GL from Akzo Nobel.

The core can optionally comprise one or more further complexing agents for alkaline earth metal ions and/or heavy metal ions, such as e.g. polymers such as polyacrylates or sulfonated polymers (for example sulfonated multipolymer such as Acusol 588 from Room and Haas (Dow)) or ethylenediaminetetraacetic acid (EDTA, for example Dissolvine NA from Akzo Nobel), in particular as tetrasodium salt.

The core particularly preferably comprises GLDA granules or co-granules (i.e. granules with auxiliaries which simplify the granulation of GLDA, e.g. polycarboxylates).

Within the context of the present invention, the expression GLDA preferably refers to glutamic acid-N,N-diacetic acid or one of the salts described herein (e.g. the tetrasodium salt).

The solid produced according to the invention comprises, as coating, preferably essentially compounds of the formula I, where small amounts of starting materials and/or by-products from the preparation of the compounds of the formula I may additionally be present. Depending on the synthesis method used, customary purities for the compounds I are 70 to 99.9% by weight, in particular 80 to 99.5% by weight, in each case based on the solids content.

For the present invention, those compounds of the formula I in which R is $C_1$- to $C_{20}$-alkyl, $C_2$- to $C_{20}$-alkenyl or a radical of the formula

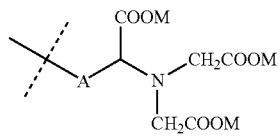

are preferably suitable.

As compound of the formula I, particular preference is given to using α-alanine-N,N-diacetic acid (R=CH$_3$, MGDA) and its salts. Preference is given to using e.g. its alkali metal salts, ammonium salts and substituted ammonium salts.

Of suitability as such salts are primarily the sodium, potassium and ammonium salts, in particular the trisodium, tripotassium and triammonium salt, and also organic triamine salts with a tertiary nitrogen atom.

Suitable bases underlying organic amine salts are in particular tertiary amines, such as trialkylamines having 1 to 4 carbon atoms in each alkyl, such as trimethyl- and triethylamine, and trialkanolamines having 2 or 3 carbon atoms in the alkanol radical, preferably triethanolamine, tri-n-propanolamine or triisopropanolamine.

The alkaline earth metal salts used are in particular the calcium and magnesium salts.

Besides methyl, of suitability for the radical R as straight-chain or branched alk(en)yl radicals, are in particular $C_2$- to $C_{17}$-alkyl and -alkenyl, here in particular straight-chain radicals derived from saturated or unsaturated fatty acids.

Examples of individual radicals R are: ethyl, n-propyl, isopropyl, n-butyl, isobutyl, sec-butyl, tert-butyl, n-pentyl, isopentyl, tert-pentyl, neopentyl, n-hexyl, n-heptyl, 3-heptyl (derived from 2-ethylhexanoic acid), n-octyl, isooctyl (derived from isononanoic acid), n-nonyl, n-decyl, n-undecyl, n-dodecyl, isododecyl (derived from isotridecanoic acid), n-tridecyl, n-tetradecyl, n-pentadecyl, n-hexadecyl, n-heptadecyl, n-octadecyl, n-nonadecyl, n-eicosyl and n-heptadecenyl (derived from oleic acid). For R, it is also possible for mixtures to arise, in particular those which are derived from naturally occurring fatty acids and from synthetically produced technical-grade acids, for example by oxo synthesis.

The $C_1$- to $C_{12}$-alkylene bridges A are in particular polymethylene groups of the formula $(CH_2)_k$, in which k is a number from 2 to 12, in particular from 2 to 8, i.e. 1,2- ethylene, 1,3-propylene, 1,4-butylene, pentamethylene, hexamethylene, heptamethylene, octamethylene, nonamethylene, decamethylene, undecamethylene and dodecamethylene. Hexamethylene, octamethylene, 1,2-ethylene and 1,4-butylene are particularly preferred here. In addition, however, branched $C_3$- to $C_{12}$-alkylene groups can also occur, e.g. —$CH_2CH(CH_3)CH_2$—, —$CH_2C(CH_3)_2CH_2$—, —$CH_2CH(C_2H_5)$— or $CH_2CH(CH_3)$—.

The $C_1$- to $C_{30}$-alkyl and $C_2$- to $C_{30}$-alkenyl groups can carry up to 5, in particular up to 3, additional substituents of the specified type and be interrupted by up to 5, in particular up to 3, nonadjacent oxygen atoms. Examples of such substituted alk(en)yl groups are —$CH_2OH$, —$CH_2CH_2OH$, —$CH_2CH_2$—O—$CH_3$, —$CH_2CH_2$—O—$CH_2CH_2$—O—$CH_3$, —$CH_2$—O—$CH_2CH_3$, —$CH_2$—O—$CH_2CH_2$—OH, —$CH_2$—CHO, —$CH_2$—OPh, —$CH_2$—$COOCH_3$ or —$CH_2CH_2$—$COOCH_3$.

Suitable alkoxy(late) groups are in particular those in which m and n, in each case independently of one another, are numbers from 0 to 30, in particular from 0 to 15. $A^1O$ and $A^2O$ are preferably groups derived from butylene oxide and in particular from propylene oxide and from ethylene oxide. Of particular interest are pure ethoxylates and pure propoxylates, but ethylene oxide-propylene oxide block structures can also arise.

Suitable five- or six-membered unsaturated or saturated heterocyclic rings having up to three heteroatoms from the group nitrogen, oxygen and sulfur, which can be additionally benzo-fused and substituted by the designated radicals, are e.g.:

tetrahydrofuran, furan, tetrahydrothiophene, thiophene, 2,5-dimethylthiophene, pyrrolidine, pyrroline, pyrrole, isoxazole, oxazole, thiazole, pyrazole, imidazoline, imidazole, 1,2,3-triazolidine, 1,2,3- and 1,2,4-triazole, 1,2,3-, 1,2,4- and 1,2,5-oxadiazole, tetrahydropyran, dihydropyran, 2H- and 4H-pyran, piperidine, 1,3- and 1,4-dioxane, morpholine, pyrazan, pyridine, α-, β- and γ-picoline, α- and γ-piperidone, pyrimidine, pyridazine, pyrazine, 1,2,5-oxathiazine, 1,3,5-, 1,2,3- and 1,2,4-triazine, benzofuran, thionaphthene, indoline, indole, isoindoline, benzoxazole, indazole, benzimidazole, chromane, isochromane, 2H- and 4H-chromene, quinoline, isoquinoline, 1,2,3,4-tetrahydroisoquinoline, cinnoline, quinazoline, quinoxaline, phthalazine and benzo-1,2,3-triazine.

N—H groups in the specified heterocyclic rings should be present as far as possible in derivatized form, for example as N-alkyl group (e.g. having 1 to 12 carbon atoms).

In the case of substitution on the phenyl rings or the heterocyclic rings, preferably two (identical or different) or in particular one individual substituent, arise.

Examples of optionally substituted phenylalkyl groups and alkyl groups carrying heterocyclic rings for R are benzyl, 2-phenylethyl, 3-phenylpropyl, 4-phenylbutyl, o-, m- or p-hydroxybenzyl, o-, m- or p-carboxylbenzyl, o-, m- or p-sulfobenzyl, o-, m- or p-methoxy or -ethoxycarbonylbenzyl, 2-furylmethyl, N-methylpiperidin-4-ylmethyl or 2-, 3- or 4-pyridinylmethyl.

For the substitution on phenyl rings and also on heterocyclic rings, preference is given to using water-solubilizing groups such as hydroxyl groups, carboxyl groups or sulfo groups. Examples of the specified $C_1$- to $C_4$-, $C_1$- to $C_{12}$- and $C_1$- to $C_{20}$-alkyl groups are also to be understood as meaning the corresponding radicals listed above for R.

The solid according to the invention is suitable to a particular degree as a component for solid detergent and cleaner formulations. Subsequently, solid detergent and cleaner formulations which comprise the solid according to the invention as complexing agent for alkaline earth metal ions and heavy metal ions in the amounts customary for this purpose, as well as other customary constituents of such formulations, are also provided by the present invention. Compositions and customary constituents of such solid detergent and cleaner formulations are known to the person skilled in the art and therefore do not need to be explained in more detail here.

The example below is intended to illustrate the invention in more detail. The glycine-N,N-diacetic acid derivative I used was α-alanine-N,N-diacetic acid (methylglycine-N,N-diacetic acid, "MGDA") trisodium salt.

EXAMPLES

The following processes were carried out on a pilot fluidized-bed spray-granulation apparatus model AGT 400 from Glatt which was equipped with a cyclone, a filter and a wet scrubber.

Example 1

It was an aim of this experiment to coat granules of GLDA with Trilon M liquid (BASF). The target grain size was 200-1000 μm. Experimental procedure and results Trilon M liquid was heated to 90-95° C. and sprayed onto the initial charge of GLDA granules. This gave granules in the desired grain spectrum. The oversize fraction was sieved off over a 1000 μm sieve.

At the following processing parameters, the coating was able to run in a stable manner:
incoming air temperature 140° C.
incoming air amount: 1400 m$^3$/h
product temperature 100-104° C.
outgoing air temperature: 98-101° C.
spraying pressure: 2.0 bar
spraying rate: ca. 350-450 g/min
storage container: 90° C.

After establishing the processing parameter specified above, it was possible to achieve a stable process.

By means of subsequent protective sieving over 1000 μm, 15.9 kg of granules were separated. The oversize fraction amounted to 6.0 kg.

Example 2

The aim of this experiment was to coat co-granules of GLDA and a polymer (homopolymer Sokalan PA 30 CL (BASF)) with Trilon M Liquid. Target grain size of the coated granules: 200-1000 μm.

10 kg of Trilon M liquid were heated to 90-95° C. and sprayed on to the initial charge of co-granules (15 kg). This gave granules in the desired grain spectrum. The oversize fraction was sieved over a 1000 μm sieve.

At the following processing parameters, the coating is able to run in a stable manner:
incoming air temperature 130-140° C.
incoming air amount: 1200 m$^3$/h
product temperature 104-106° C.
outgoing air temperature: 100-102° C.
spraying pressure: 2.0 bar
spraying rate: ca. 100-150 g/min
storage container: 95° C.

The following example amounts were prepared:
17.0 kg of granules (sieved over 1000 μm). The oversize fraction was 5.1 kg.

After establishing the processing parameters given above, it was possible to achieve a stable process.

Example 3

The aim of this experiment was to coat co-granules of GLDA and a polymer (homopolymer Sokalan PA 30 CL (BASF)) with Trilon M Liquid. Target grain size of the coated granules: 200-1000 μm.

20 kg of Trilon M liquid were heated to 90-95° C. and sprayed on to the initial charge of co-granules (15 kg). This gave granules in the desired grain spectrum. The oversize fraction was sieved over a 1000 μm sieve.

At the following processing parameters, the coating is able to run in a stable manner:
incoming air temperature 130-140° C.
incoming air amount: 1200 m³/h
product temperature 104-106° C.
outgoing air temperature: 100-102° C.
spraying pressure: 2.0 bar
spraying rate: ca. 100-150 g/min
storage container: 95° C.

The following example amounts were prepared:
20.3 kg of granules (sieved over 1000 μm). The oversize fraction was 5.2 kg.

After establishing the processing parameters given above, it was possible to achieve a stable process.

The invention claimed is:

1. A solid, comprising:
   (1) a core comprising at least one selected from the group consisting of glutamic acid-N,N-diacetic acid, a salt of glutamic acid-N,N-diacetic acid, and a derivative thereof; and
   (2) a coating comprising a compound of formula (I):

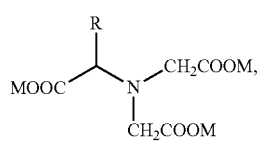

(I)

wherein:
R represents
a $C_1$- to $C_{30}$-alkyl or $C_2$- to $C_{30}$-alkenyl, additionally substituted with up to 5 hydroxyl groups, formyl groups, $C_1$- to $C_4$-alkoxy groups, phenoxy groups or $C_1$- to $C_4$-alkoxycarbonyl groups, and optionally interrupted by up to 5 nonadjacent oxygen atoms,
an alkoxylate group of the formula (Ia):

(Ia), wherein
$A^1$ and $A^2$, independently, represent 1,2-alkylene groups having 2 to 4 carbon atoms,
Y represents hydrogen, $C_1$- to $C_{12}$-alkyl, phenyl or $C_1$- to $C_4$-alkoxycarbonyl,
k represents the number 1, 2 or 3, and
m and n, independently, represent a number from 0 to 50, such that a sum of m+n is at least 4,
a phenylalkyl group having 1 to 20 carbon atoms in the alkyl,
a five- or six-membered unsaturated or saturated heterocyclic ring having up to three heteroatoms selected from the group consisting of nitrogen, oxygen and sulfur, optionally benzo-fused,
such that all of the phenyl rings and heterocyclic rings specified in the meanings for R are optionally substituted with up to three $C_1$- to $C_4$-alkyl groups, hydroxyl groups, carboxyl groups, sulfo groups, $C_1$- to $C_4$-alkoxycarbonyl groups, or mixtures thereof, or a radical of for the formula (Ib):

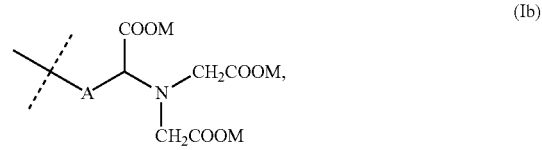

(Ib)

wherein A represents a $C_1$- to $C_{12}$-alkylene bridge or a chemical bond; and
each M, independently, represents hydrogen, alkali metal, alkaline earth metal, ammonium or substituted ammonium, in corresponding stoichiometric amounts.

2. The solid according to claim 1, wherein R represents $C_1$- to $C_{20}$-alkyl, $C_2$- to $C_{20}$-alkenyl or a radical of formula (Ib):

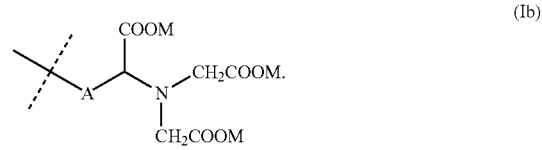

(Ib)

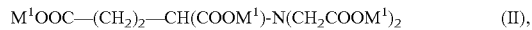

3. The solid according to claim 1, wherein the coating (2) consists essentially of α-alanine-N,N-diacetic acid or its alkali metal, ammonium or substituted amine salts.

4. The solid according to claim 1, wherein the core (1) comprises a compound of formula (II):

$$M^1OOC—(CH_2)_2—CH(COOM^1)\text{-}N(CH_2COOM^1)_2 \quad (II),$$

wherein $M^1$ represents at least one selected from the group consisting of hydrogen, ammonium, an alkali metal, and an organic amine.

5. A method for producing the solid according to claim 1, the method comprising:
   initially introducing a seed in the form of a solid comprising at least one selected from the group consisting of glutamic acid-N,N-diacetic acid, a salt of glutamic acid-N,N-diacetic acid, and a derivative thereof; and
   spray-granulating the seed with at least one compound of the formula (I) to form a coating.

6. The method according to claim 5, wherein the spray-granulating is with an aqueous solution of the at least one compound of the formula (I).

7. A solid detergent or cleaner formulation, comprising the solid according to claim 1 as a complexing agent for alkaline earth metal ions and heavy metal ions.

8. The solid according to claim 2, wherein the coating (2) consists essentially of α-alanine-N,N-diacetic acid or its alkali metal, ammonium or substituted amine salts.

9. The solid according to claim 2, wherein where the core (1) comprises a compound of formula (II):

$$M^1OOC—(CH_2)_2—CH(COOM^1)\text{-}N(CH_2COOM^1)_2 \quad (II),$$

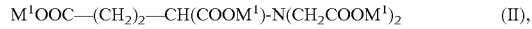

wherein $M^1$ represents at least one selected from the group consisting of hydrogen, ammonium, an alkali metal, and an organic amine.

10. A method for producing the solid according to claim 2, the method comprising:

initially introducing a seed in the form of a solid comprising at least one selected from the group consisting of glutamic acid-N,N-diacetic acid, a salt of glutamic acid-N,N-diacetic acid, and a derivative thereof; and spray-granulating the seed with at least one compound of the formula (I) to form a coating.

11. The method according to claim 10, wherein the spray-granulating is with an aqueous solution of the at least one compound of the formula (I).

12. A solid detergent or cleaner formulation, comprising the solid according to claim 2 as a complexing agent for alkaline earth metal ions and heavy metal ions.

\* \* \* \* \*